(12) United States Patent
Ouchi (10) Patent No.: US 7,611,457 B2
(45) Date of Patent: Nov. 3, 2009

(54) FRONT END STRUCTURE OF ENDOSCOPE (75) Inventor: Teruo Ouchi, Saitama (JP)

(73) Assignee: Hoya Corporation, Tokyo (JP)

( * ) Notice: Subject to any disclaimer, the term of this patent is extended or adjusted under 35 U.S.C. 154(b) by 388 days.

(21) Appl. No.: 11/331,177

(22) Filed: Jan. 13, 2006

(65) Prior Publication Data

US 2006/0161046 A1   Jul. 20, 2006

(30) Foreign Application Priority Data

Jan. 14, 2005   (JP)   ............................. 2005-006979

(51) Int. Cl.
*A61B 1/00* (2006.01)
*A61B 1/06* (2006.01)

(52) U.S. Cl. .................. 600/129; 600/127; 600/175

(58) Field of Classification Search ................ 600/118, 600/127, 129, 139, 146, 149, 175; 604/95.03, 604/103.08, 160
See application file for complete search history.

(56) References Cited

U.S. PATENT DOCUMENTS 4,881,810 A * 11/1989 Hasegawa ................ 356/241.5
5,685,823 A * 11/1997 Ito et al. ................... 600/127
5,897,487 A *  4/1999 Ouchi ....................... 600/127
5,976,073 A    11/1999 Ouchi
6,149,659 A * 11/2000 Ahmed ..................... 606/140
6,676,672 B2 *  1/2004 Chu et al. .................. 606/139
7,413,543 B2 *  8/2008 Banik et al. ............... 600/129

FOREIGN PATENT DOCUMENTS

JP   10-248792    9/1998
JP   2002-125915  5/2002

OTHER PUBLICATIONS

English Language Abstract of JP 10-248792.
English Language Abstract of JP 2002-125915.
U.S. Appl. No. 11/331,168 to Ouchi, filed on Jan. 13, 2006.

* cited by examiner

*Primary Examiner*—Linda C Dvorak
*Assistant Examiner*—Alireza Nia
(74) *Attorney, Agent, or Firm*—Greenblum & Bernstein P.L.C.

(57) ABSTRACT

An endoscope having an inserted portion, which is to be inserted into a tubular organ, including a bendable portion that is adapted to bend arbitrarily by a remote operation and a distal unit with a window for observation to capture an image of inside the tubular organ, is provided. A plurality of grooves are formed in parallel with an axis of the distal unit on a circumferential surface of the distal unit and the grooves are spaced from each other.

9 Claims, 8 Drawing Sheets

FRONT END STRUCTURE OF ENDOSCOPE

BACKGROUND OF THE INVENTION

The present invention relates to an endoscope to be inserted into a tubular organ including a large intestine.

When an endoscope is inserted into a tubular organ such as a large intestine through an anus, an inserted portion of the endoscope proceeds in the winding intestine through a relatively short rectum, an S-shaped sigmoid colon with a small curvature, a descending colon and a traverse colon until the inserted portion reaches to an ascending colon. Specifically, a part of the intestine between the descending colon and the traverse colon is bent at an angle that is generally sharper than the right angle, therefore it has been difficult for operators to insert the endoscope deeply in the colons.

In addition, most part of the colons is movable in a body cavity and not held to a body wall, thus the colons, specifically the sigmoid colon, are easily elongated, shortened or deformed by external force. Therefore, even if the endoscope is forcibly inserted into the colons, the colons are merely elongated by the inserted portion, and the inserted portion is not effectively advanced deeply in the colons.

In consideration of the above problems, when the inserted portion is inserted in the colons and advanced to an extent, a bendable portion of the endoscope, which is configured at a distal end of the inserted portion, is bent at a small curvature by a remote operation from the operator, and the distal end is pressed and hooked to a creased portion of an inner wall of the colon. With the distal end hooked to the crease, the inserted portion is twisted in a circumferential direction along with the inserted portion, thus the colon is turned to be partially straightened so that the inserted portion can be advanced further with respect to the colon.

Such an endoscope for a large intestine with the inserted portion and the bendable portion is generally provided with an observation window at the distal end for capturing an image of an object, which is ahead of the inserted portion. In such case, the inserted portion is often provided further with a hood that protrudes from an outer edge of the inserted portion to prevent the observation window from directly being in contact with an intestinal wall. An example of such an endoscope is disclosed in Japanese Patent Provisional Publication HEI10-248792. In recent years, there are also provided with endoscopes having observation windows and no hoods. An example of such an endoscope is disclosed in Japanese Patent Provisional Publication 2002-125915.

When an endoscope as described above is inserted into the colons and twisted to partially straighten the colon, the bendable portion hooked to the crease may slip and be unhooked from the crease unintentionally. In such case, the operator is required to repeat the hooking and twisting operations, which consume time and may be troublesome.

SUMMARY OF THE INVENTION

Aspects of the present invention are advantageous in that an endoscope having an inserted portion, which is to be inserted into a tubular organ, including a bendable portion that is adapted to bend arbitrarily by a remote operation and a distal unit with a window for observation to capture an image of inside the tubular organ, is provided. A plurality of grooves are formed in parallel with an axis of the distal unit on a circumferential surface of the distal unit and the grooves are spaced from each other.

An outer diameter of the distal unit may be configured to be greater than an outer diameter of the bendable portion. A step may be formed at a boundary of the bendable portion and the distal unit. The circumferential surface of the distal unit may be provided with the plurality of grooves.

The circumferential surface of the distal unit may formed to be tapered. The circumferential surface of the distal unit may be provided with the plurality of grooves.

A cross-sectional shape of each of the plurality of grooves may be an arc.

Aspects of the present invention are advantageous in that an endoscope having an inserted portion, which is to be inserted into a tubular organ, including a bendable portion that is adapted to bend arbitrarily by a remote operation and a distal unit with a window for observation to capture an image of inside the tubular organ is provided. The distal unit is provided with a tubular hood that protrudes forwardly from an edge of the distal unit. A plurality of grooves are formed perpendicularly to a diameter of the hood and the grooves are spaced from each other.

An outer diameter of the hood may be configured to be greater than an outer diameter of the bendable portion. The circumferential surface of the hood may be provided with the plurality of grooves.

DETAILED DESCRIPTION OF THE EMBODIMENT

Referring to the accompanying drawings, an endoscope according to an embodiment of the invention will be described in detail.

First Embodiment

Figure 4:
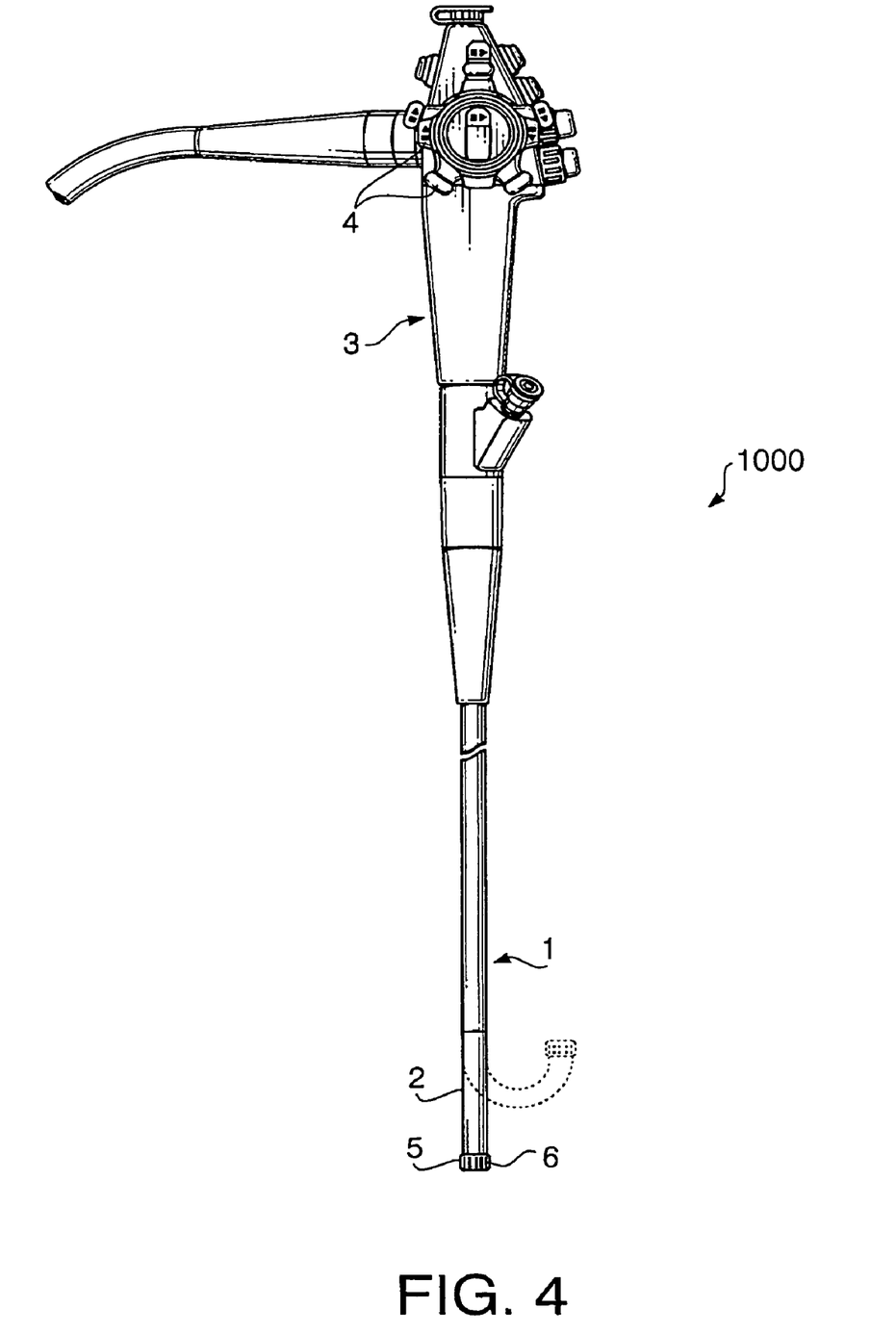
FIG. 4 is an external view of the entire configuration of the endoscope according to the first embodiment of the present invention.

FIG. 4 is an external view of an entire configuration of an endoscope 1000 according to a first embodiment of the present invention. The endoscope 1000 is provided with a flexible inserted portion 1. The inserted portion 1 includes a bendable portion 2 in a vicinity to a distal end of the endoscope 1000. The endoscope 1000 is further provided with an operation unit 3 that is attached to the proximal end of the inserted portion 1 and operation knobs 4. The bendable portion 2 is configured to bend at an arbitrary curvature in an arbitrary direction, for example as shown in the dotted lines in FIG. 4, by an operation to the operation knobs 4.

At the distal end of the endoscope 1000, the bendable portion 2 is provided with an inflexible and short column-like distal unit 5, in which various functional components for example an optical system and a solid-state image capturing element are installed. On an outer peripheral surface of the distal unit 5, a plurality of grooves 6, which are spaced from each other, are formed in parallel with an axial direction of the distal unit 5.

Figure 1:
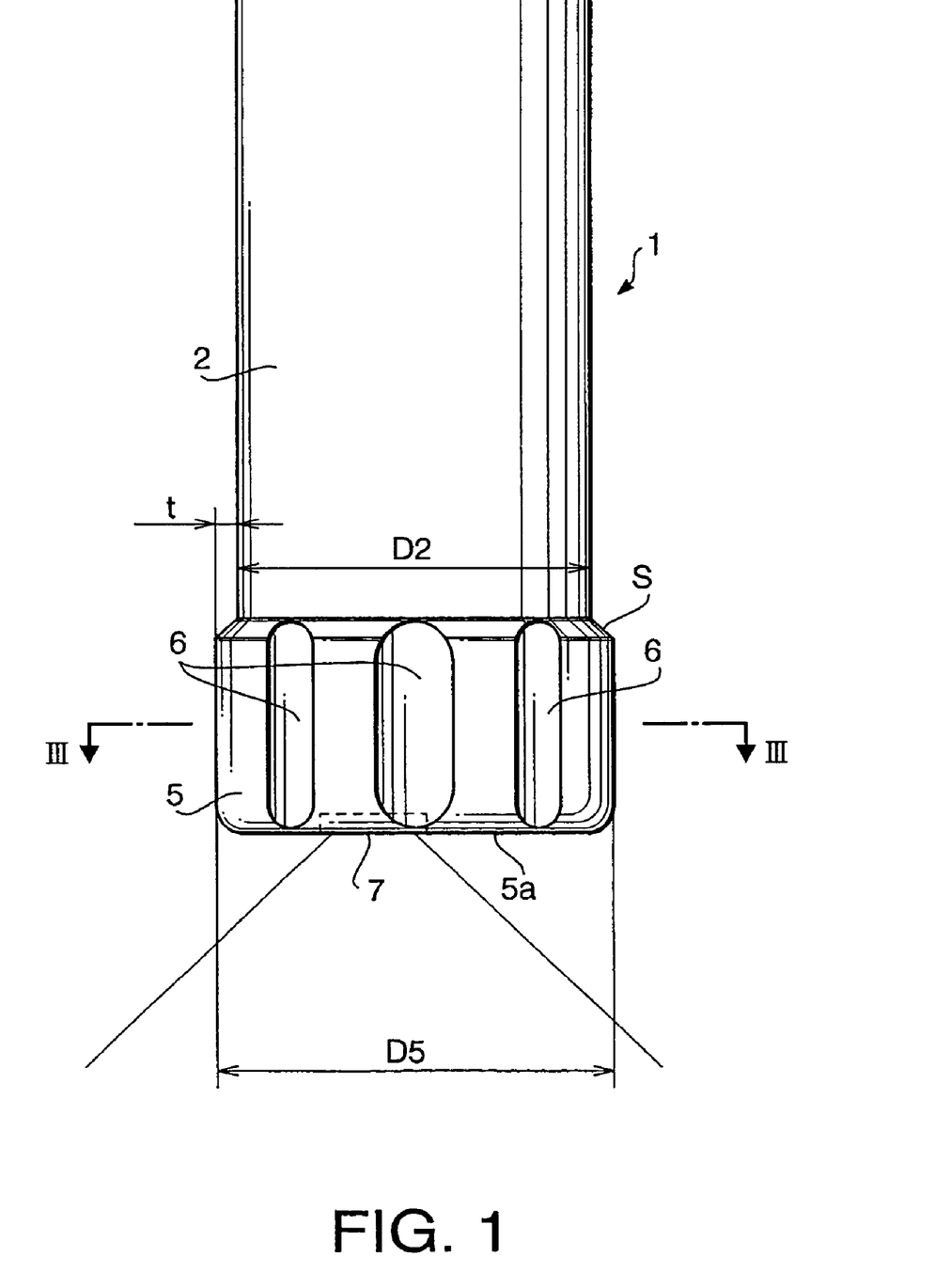
FIG. 1 is a side view of an inserted portion of an endoscope according to a first embodiment of the present invention.
Figure 2:
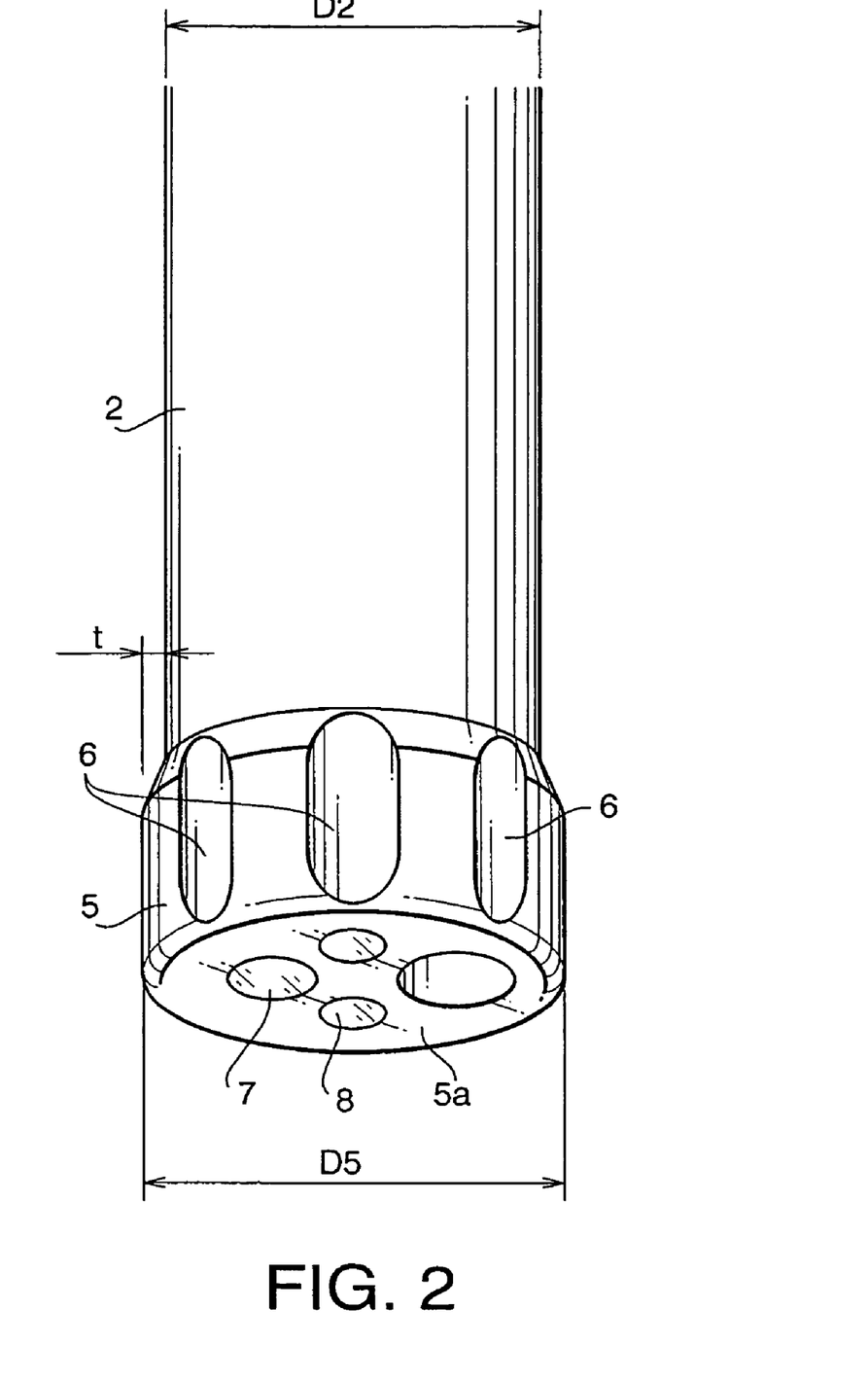
FIG. 2 is a perspective view of the inserted portion of the endoscope according to the first embodiment of the present invention.

FIG. 1 is a side view of the inserted portion 1 with the distal unit 5 of the endoscope 1000 according to the first embodiment of the present invention, and FIG. 2 is a perspective view of the inserted portion 1 and the distal unit 5 of the endoscope 1000 according to the first embodiment of the present invention. On a distal surface 5a of the distal unit 5, a plurality of windows including an observation window 7 and an illumination window 8 to capture an image of an object are provided, so that the operator can observe inside of the colons.

An outer diameter D5 of the distal unit 5 is configured to be greater than an outer diameter D2 of the bendable portion 2 (more specifically, the diameter of the bendable portion 2 at the closest to the distal unit 5). Therefore, a step S is circumferentially formed at a boundary between the distal unit 5 and the bendable portion 2. A depth t of the step S is for example in a range from 0.5 mm to 2 mm.

Figure 3:
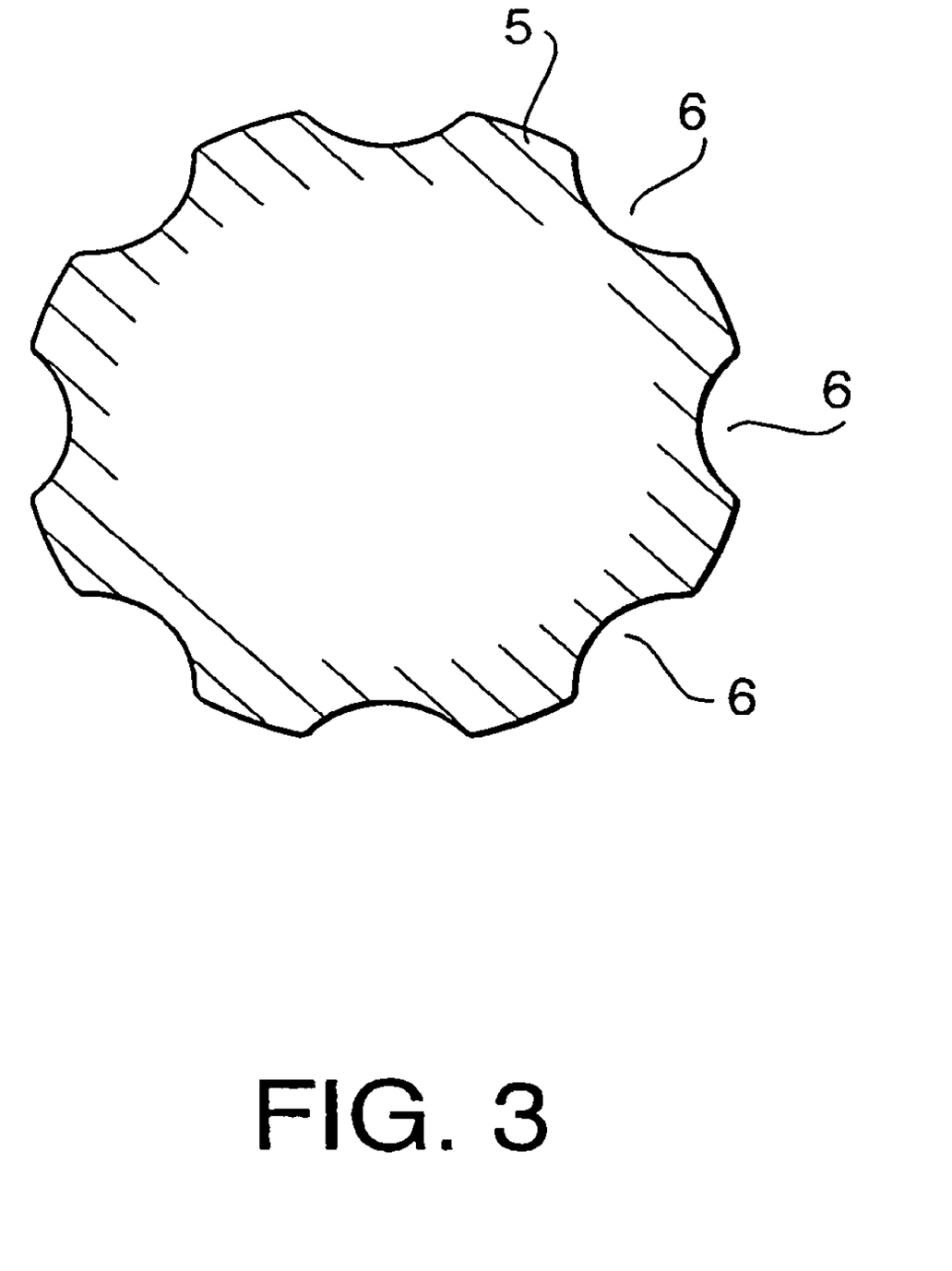
FIG. 3 is a cross-sectional view of a distal unit of the endoscope taken along the line III-III in FIG. 1.

FIG. 3 is a cross-sectional view of the distal unit 5 of the endoscope 1000 taken along the line III-III in FIG. 1. As shown in FIG. 3, evenly spaced eight grooves 6 are formed on the outer peripheral surface of the distal unit 5, although the grooves 6 are not necessarily spaced evenly from each other. Each groove 6 is curved to have a cross-sectional shape of an arc. However, it should be noted that the cross sectional shape of each groove 6 is not limited to an arc. A depth of each groove 6 from the outer peripheral surface of the distal unit 5 is configured to be substantially equal to the depth t of the step S. It should be also noted that the number of the grooves 6 is not limited to eight, but is preferable to be in a range from three to twelve for practical reasons.

Figure 5:
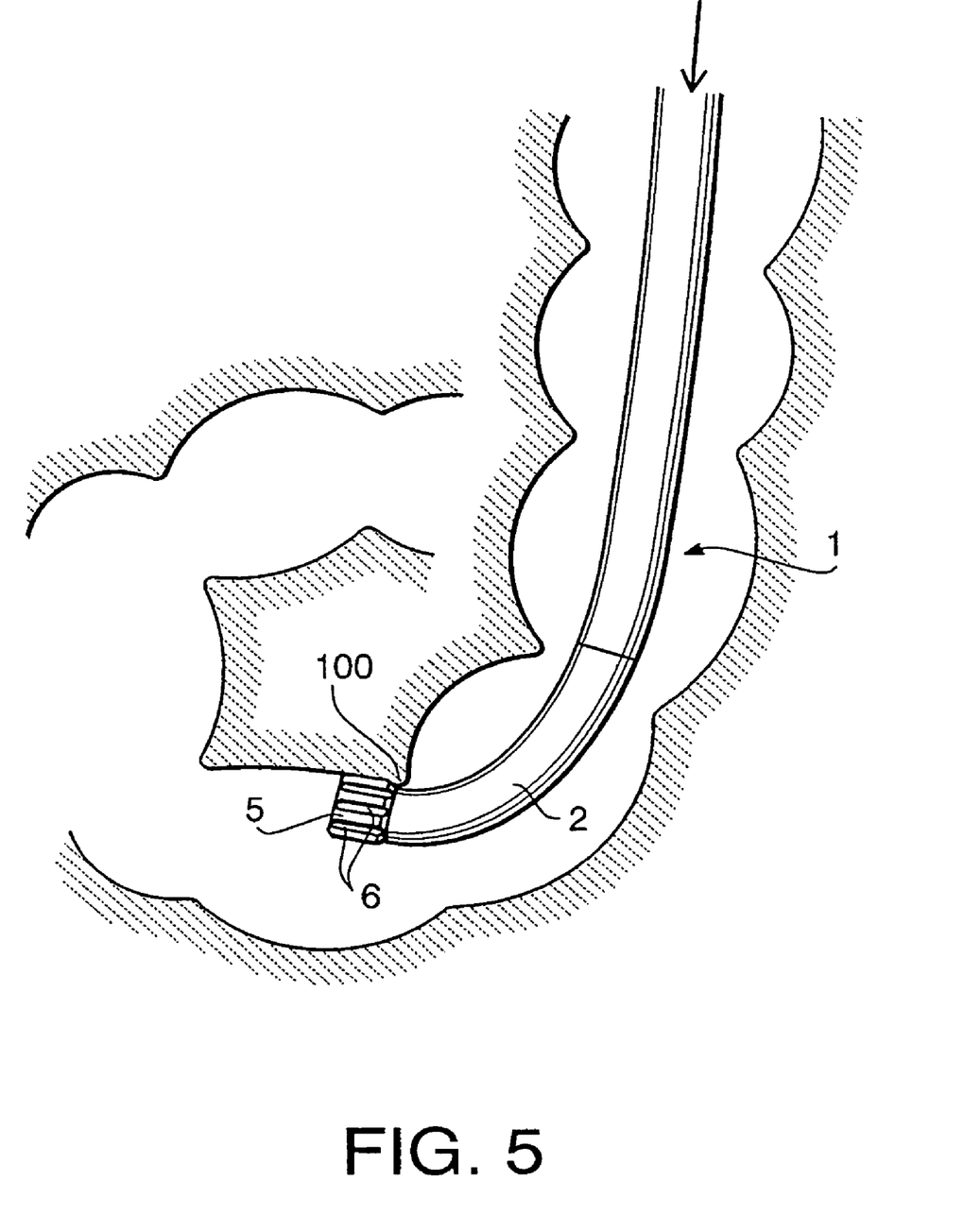
FIG. 5 is an illustrative view of the endoscope in use according to the first embodiment of the present invention.

FIG. 5 is an illustrative view of the endoscope 1000 in use according to the first embodiment of the present invention. The bendable portion 2 with the distal unit that passed by a crease 100 is bent by a remote operation, and the grooves 6 of the distal unit 5 are pressed and hooked to a back surface of the crease 100.

Figure 6:
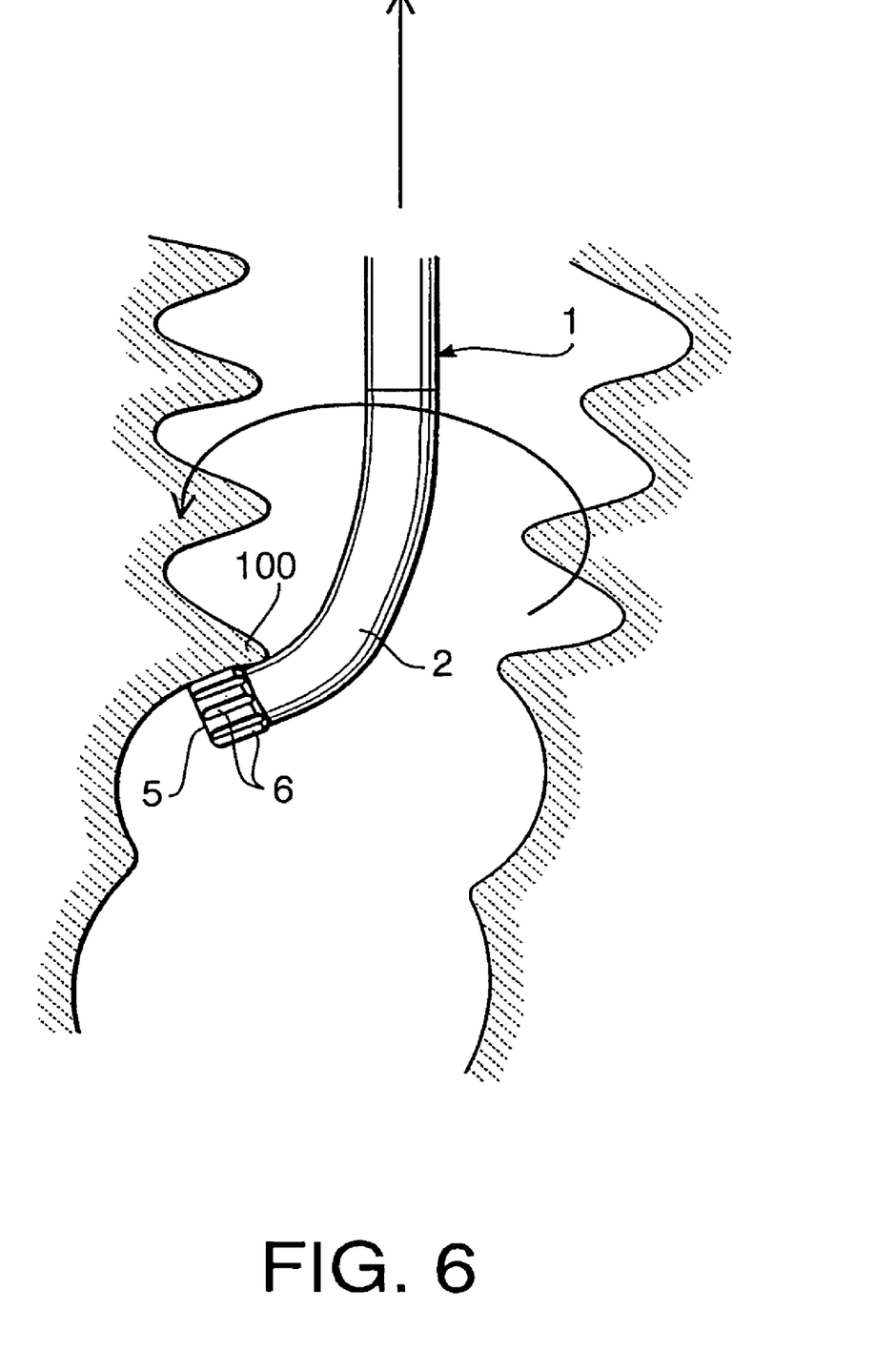
FIG. 6 is another illustrative view of the endoscope in use according to the first embodiment of the present invention.

FIG. 6 is another illustrative view of the endoscope 1000 in use according to the first embodiment of the present invention. With the grooves 6 hooked to the crease 100, when the inserted portion 1 is twisted in the circumferential direction, for example as indicated by an arrow in FIG. 6, the looped colon is turned along with the inserted portion 1 to be partially straightened. In addition, the crease 100 hooked with an edge of the step S can be pulled toward the anus, thus the colon toward the anus can be partially shortened, and the trailed part of the colon is straightened, so that the inserted portion 1 can be further advanced with respect to the colon.

In the above-described operation, the distal unit 5 with the grooves 6 of the endoscope of the present invention is firmly hooked to the crease 100, and the distal unit 5 is less likely to be detached from the crease 100. Therefore, the colons are effectively straightened and the inserted portion 1 can be securely advanced in the colons.

Second Embodiment

Figure 7:
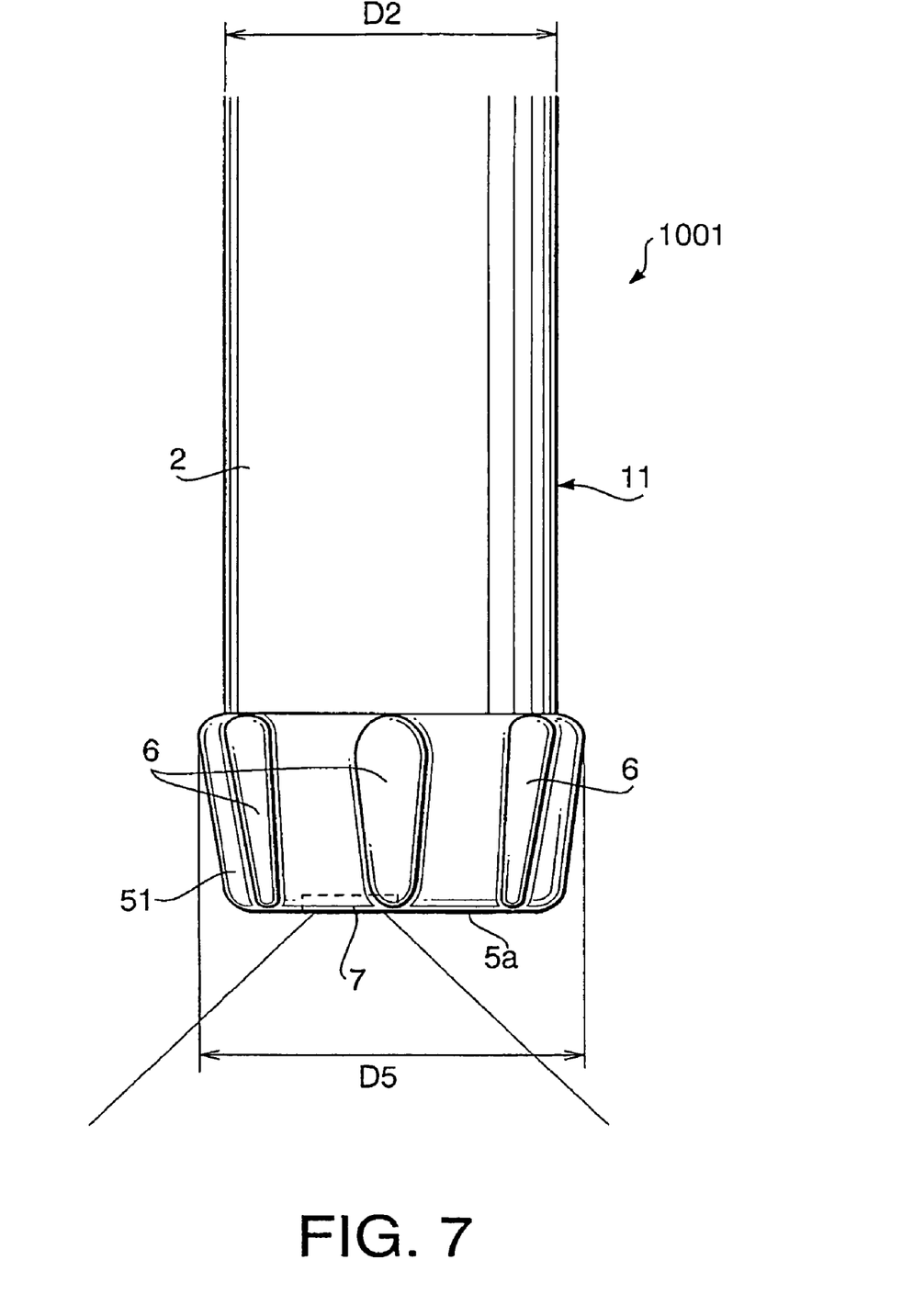
FIG. 7 is a side view of an inserted portion of an endoscope according to a second embodiment of the present invention.

FIG. 7 is a side view of the inserted portion 11 of an endoscope 1001 according to a second embodiment of the present invention. A circumferential surface of a distal unit 51 in the second embodiment is configured to be tapered with an outer diameter at an distal end of the distal unit 51 being smaller than an outer diameter D5' at a boundary between the distal unit 51 and an inserted portion 11. With this configuration, inserting the distal unit 51 in the colons becomes easier than inserting the distal unit 5 of the first embodiment. The remaining configuration of the endoscope 1001 is similar to the configuration of the first embodiment.

Third Embodiment

Figure 8:
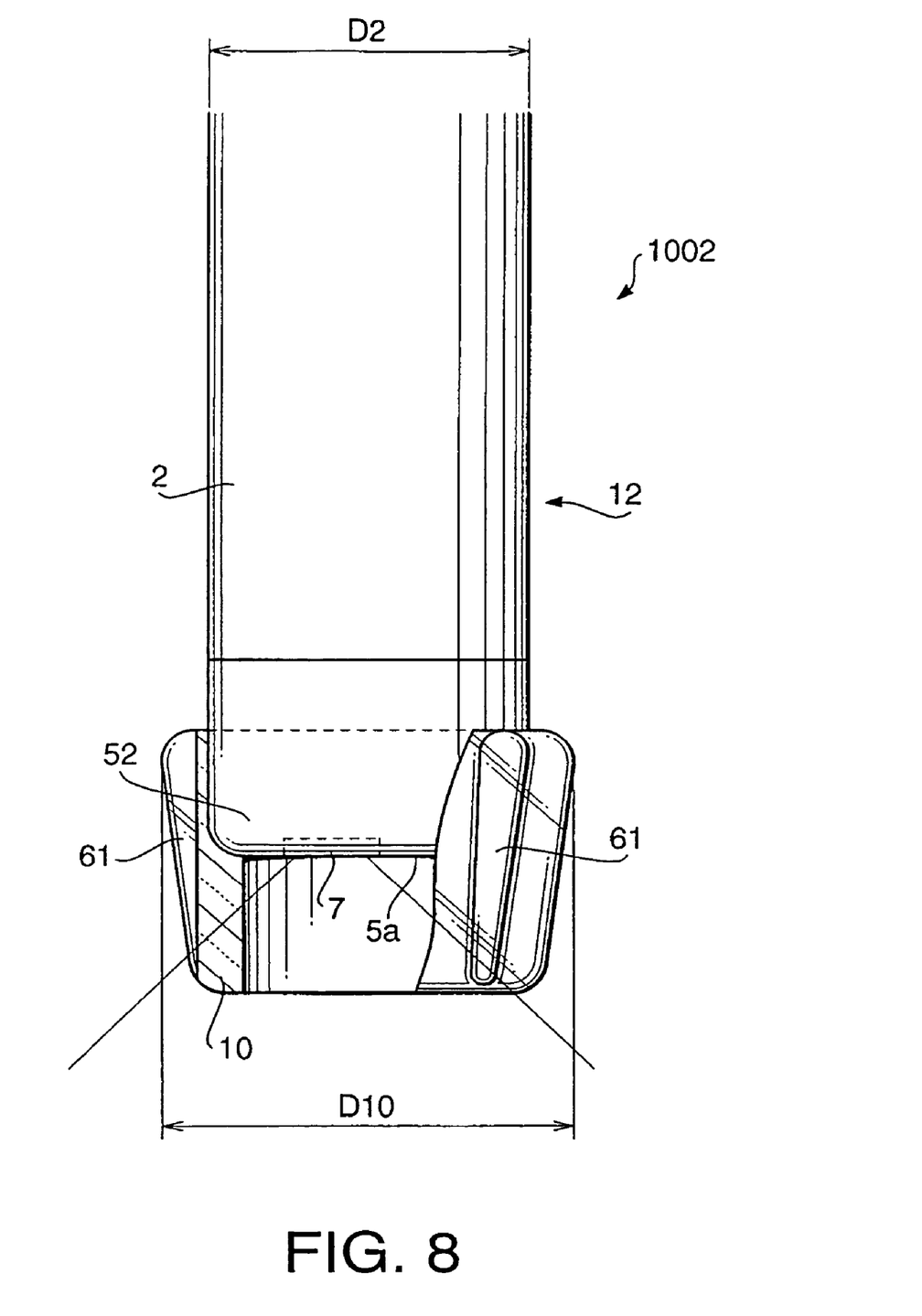
FIG. 8 is a partially cross-sectional view of an inserted portion of an endoscope according to a third embodiment of the present invention.

FIG. 8 is a partially cross-sectional view of an inserted portion 12 of an endoscope 1002 according to a third embodiment of the present invention. A hood 10 is detachably attached to a distal unit 52. The hood 10 may be attached to the distal unit 52 by being elastically tightened, engaged by an engaging structure including a pair of an engaging protrusion and a mating recessed portion, screwed to the distal unit 52, or in other known configurations. The hood 10 is configured to protrude forwardly from an edge of the distal unit 52.

On a circumferential surface of the hood 10, a plurality of grooves 61, are formed perpendicularly to a diameter of the hood 10 and spaced from each other. Each of the grooves 61 is curved to have a cross-sectional shape of an arc. However, it should be noted that the cross sectional shape of each groove 61 is not limited to an arc. Further, an outer diameter D10 of the hood 10 is configured to be greater than an outer diameter D2 of the bendable portion 2. With this configuration, the endoscope 1002 is capable of effectively straightening the colons and is securely advanced in the colons. The hood 10 may be formed with a transparent material, in which case a scope for observation is not intercepted by the hood 10.

The present disclosure relates to the subject matter contained in Japanese Patent Application No. 2005-006979, filed on Jan. 14, 2005, which is expressly incorporated herein by reference in its entirety.

What is claimed is:

1. An endoscope comprising:
    an inserted portion, which is to be inserted into a tubular organ, including a bendable portion that is adapted to bend arbitrarily by a remote operation and a distal unit with a window for observation to capture an image of inside the tubular organ,
    wherein a plurality of grooves are formed in parallel with an axis of the distal unit on an outer peripheral surface of the distal unit and extend entirely across the axis along the outer peripheral surface of the distal unit, and are spaced from each other, each of the plurality of grooves having a depth,
    wherein the distal unit is configured to hook a crease of an organ and to advance the inserted portion,
    wherein an outer diameter of the distal unit is configured to be greater than an outer diameter of the bendable portion,
    wherein a step having a height is formed at a boundary of the bendable portion and the distal unit, and
    wherein the depth of each of the plurality of grooves is equal to the height of the step.

2. The endoscope according to claim 1, wherein a circumferential surface of the distal unit is formed to be tapered.

3. The endoscope according to claim 1, wherein a cross-sectional shape of each of the plurality of grooves is an arc.

4. An endoscope comprising:
    an inserted portion, which is to be inserted into a tubular organ, including a bendable portion that is adapted to bend arbitrarily by a remote operation and a distal unit with a window for observation to capture an image of inside the tubular organ, wherein the distal unit is provided with a tubular hood that protrudes forwardly from an edge of the distal unit, wherein a plurality of grooves are formed perpendicularly to a diameter of the tubular hood and extend entirely along an outer peripheral surface of the tubular hood, and are spaced from each other, each of the plurality of grooves having a depth, wherein the tubular hood is configured to hook a crease of an organ and to advance the inserted portion, wherein an outer diameter of the tubular hood is configured to be greater than an outer diameter of the bendable portion, wherein a step having a height is formed at a boundary of the bendable portion and the tubular hood, and wherein the depth of each of the plurality of grooves is equal to the height of the step.

5. The endoscope according to claim 4, wherein a cross-sectional shape of each of the plurality of grooves is an arc.

6. The endoscope according to claim 1, wherein the height of the step is between 0.5 mm to 2 mm.

7. The endoscope according to claim 1, wherein the plurality of grooves formed on the outer peripheral surface of the distal unit is between three grooves and twelve grooves.

8. The endoscope according to claim 4, wherein the height of the step is between 0.5 mm to 2 mm.

9. The endoscope according to claim 4, wherein the plurality of grooves formed on the outer peripheral surface of the tubular hood is between three grooves and twelve grooves.

* * * * *